United States Patent
Sigg et al.

(10) Patent No.: US 9,943,633 B2
(45) Date of Patent: Apr. 17, 2018

(54) SYSTEM AND METHOD TO REGULATE ULTRAFILTRATION

(71) Applicant: Medtronic, Inc., Minneapolis, MN (US)

(72) Inventors: Daniel C. Sigg, Saint Paul, MN (US); Sarah Anne Audet, Shoreview, MN (US); Tommy D. Bennett, Shoreview, MN (US); Dwight H. Warkentin, Arden Hills, MN (US)

(73) Assignee: Medtronic Inc., Minneapolis, MN (US)

( * ) Notice: Subject to any disclaimer, the term of this patent is extended or adjusted under 35 U.S.C. 154(b) by 2 days.

(21) Appl. No.: 15/190,553

(22) Filed: Jun. 23, 2016

(65) Prior Publication Data
US 2016/0331884 A1 Nov. 17, 2016

Related U.S. Application Data

(62) Division of application No. 12/571,127, filed on Sep. 30, 2009, now Pat. No. 9,399,091.

(51) Int. Cl.
*A61M 37/00* (2006.01)
*A61M 1/34* (2006.01)
(Continued)

(52) U.S. Cl.
CPC ............ *A61M 1/3403* (2014.02); *A61M 1/16* (2013.01); *A61M 1/34* (2013.01); *A61M 1/341* (2014.02); *A61M 1/3669* (2013.01); *A61M 2205/18* (2013.01); *A61M 2205/3334* (2013.01); *A61M 2205/3344* (2013.01);
(Continued)

(58) Field of Classification Search
CPC ...... A61M 1/3403; A61M 1/341; A61M 1/16; A61M 1/34; A61M 1/3669; A61M 2205/18; A61M 2205/3334; A61M 2205/3344; A61M 2205/3523; A61M 2205/502; A61M 2205/52
See application file for complete search history.

(56) References Cited

U.S. PATENT DOCUMENTS

| 3,608,729 A | 9/1971 | Haselden |
| 3,669,878 A | 6/1972 | Marantz |

(Continued)

FOREIGN PATENT DOCUMENTS

| CN | 0101193667 | 6/2008 |
| CN | 103037917 | 4/2013 |

(Continued)

OTHER PUBLICATIONS

Office Action in Chinese Application No. 201510593695.3 dated Jul. 12, 2017.

(Continued)

*Primary Examiner* — Philip R Wiest
(74) *Attorney, Agent, or Firm* — Roger Hahn; Kenneth Collier (57) ABSTRACT

A medical device system including a physiological sensor and ultrafiltration unit senses a physiological signal in a patient and computes a fluid status measurement of the patient using the physiological signal. Ultrafiltration therapy is delivered to the patient according to a therapy delivery control parameter established in response to the fluid status measurement.

21 Claims, 6 Drawing Sheets

(51) Int. Cl.
  *A61M 1/16*  (2006.01)
  *A61M 1/36*  (2006.01)
(52) U.S. Cl.
  CPC .............. *A61M 2205/3523* (2013.01); *A61M 2205/502* (2013.01); *A61M 2205/52* (2013.01); *A61M 2230/005* (2013.01); *A61M 2230/04* (2013.01); *A61M 2230/20* (2013.01); *A61M 2230/201* (2013.01); *A61M 2230/30* (2013.01); *A61M 2230/65* (2013.01)

(56) References Cited

U.S. PATENT DOCUMENTS

| | | | |
|---|---|---|---|
| 3,669,880 A | 6/1972 | Marantz | |
| 3,850,835 A | 11/1974 | Marantz | |
| 3,884,808 A | 5/1975 | Scott | |
| 3,989,622 A | 11/1976 | Marantz | |
| 4,060,485 A | 11/1977 | Eaton | |
| 4,371,385 A | 2/1983 | Johnson | |
| 4,374,382 A | 2/1983 | Markowitz | |
| 4,381,999 A | 5/1983 | Boucher | |
| 4,460,555 A | 7/1984 | Thompson | |
| 4,556,063 A | 12/1985 | Thompson | |
| 4,562,751 A | 1/1986 | Nason | |
| 4,581,141 A | 4/1986 | Ash | |
| 4,650,587 A | 3/1987 | Polak | |
| 4,678,408 A | 7/1987 | Mason | |
| 4,685,903 A | 8/1987 | Cable | |
| 4,750,494 A | 6/1988 | King | |
| 4,826,663 A | 5/1989 | Alberti | |
| 4,828,693 A | 5/1989 | Lindsay | |
| 5,080,653 A | 1/1992 | Voss | |
| 5,092,886 A | 3/1992 | Dobos-Hardy | |
| 5,097,122 A | 3/1992 | Coiman | |
| 5,127,404 A | 7/1992 | Wyborny | |
| 5,284,470 A | 2/1994 | Beltz | |
| 5,302,288 A | 4/1994 | Meidl | |
| 5,305,745 A | 4/1994 | Zacouto | |
| 5,318,750 A | 6/1994 | Lascombes | |
| 5,468,388 A | 11/1995 | Goddard | |
| 5,507,723 A | 4/1996 | Keshaviah | |
| 5,651,893 A | 7/1997 | Kenley | |
| 5,683,432 A | 11/1997 | Goedeke | |
| 5,744,031 A | 4/1998 | Bene | |
| 5,762,782 A | 6/1998 | Kenley | |
| 5,902,336 A * | 5/1999 | Mishkin | A61F 2/064 604/27 |
| 5,944,684 A | 8/1999 | Roberts | |
| 6,048,732 A | 4/2000 | Anslyn | |
| 6,052,622 A | 4/2000 | Holmstrom | |
| 6,058,331 A | 5/2000 | King | |
| 6,156,002 A | 12/2000 | Polaschegg | |
| 6,230,059 B1 | 5/2001 | Duffin | |
| 6,248,093 B1 | 6/2001 | Moberg | |
| 6,254,567 B1 | 7/2001 | Treu | |
| 6,321,101 B1 | 11/2001 | Holmstrom | |
| 6,362,591 B1 | 3/2002 | Moberg | |
| 6,363,279 B1 | 3/2002 | Ben-Haim | |
| 6,505,075 B1 | 1/2003 | Weiner | |
| 6,554,798 B1 | 4/2003 | Mann | |
| 6,555,986 B2 | 4/2003 | Moberg | |
| 6,589,229 B1 | 7/2003 | Connelly | |
| 6,602,399 B1 | 8/2003 | Fromherz | |
| 6,627,164 B1 | 9/2003 | Wong | |
| 6,676,608 B1 | 1/2004 | Keren | |
| 6,689,083 B1 | 2/2004 | Gelfand | |
| 6,706,007 B2 | 3/2004 | Gelfand | |
| 6,711,439 B1 | 3/2004 | Bradley | |
| 6,726,647 B1 | 4/2004 | Sternby | |
| 6,780,322 B1 | 8/2004 | Bissler | |
| 6,818,196 B2 | 11/2004 | Wong | |
| 6,878,283 B2 | 4/2005 | Thompson | |
| 6,887,214 B1 | 5/2005 | Levin | |
| 6,890,315 B1 | 5/2005 | Levin | |
| 6,960,179 B2 | 11/2005 | Gura | |
| 7,074,332 B2 | 7/2006 | Summerton | |
| 7,077,819 B1 | 7/2006 | Goldau | |
| 7,131,956 B1 | 11/2006 | Pirazzoli | |
| 7,175,809 B2 | 2/2007 | Gelfand | |
| 7,208,092 B2 | 4/2007 | Micheli | |
| 7,276,042 B2 | 10/2007 | Polaschegg | |
| 7,399,289 B2 | 7/2008 | Gelfand | |
| 7,500,958 B2 | 3/2009 | Asbrink | |
| 7,566,432 B2 | 7/2009 | Wong | |
| 7,575,564 B2 | 8/2009 | Childers | |
| 7,674,231 B2 | 3/2010 | McCombie | |
| 7,704,361 B2 | 4/2010 | Garde | |
| 7,736,507 B2 | 6/2010 | Wong | |
| 7,744,553 B2 | 6/2010 | Kelly | |
| 7,754,852 B2 | 7/2010 | Burnett | |
| 7,756,572 B1 | 7/2010 | Fard | |
| 7,775,983 B2 | 8/2010 | Zhang | |
| 7,775,986 B2 * | 8/2010 | Roeher | A61M 1/34 600/483 |
| 7,776,210 B2 | 8/2010 | Rosenbaum | |
| 7,785,463 B2 | 8/2010 | Bissler | |
| 7,794,141 B2 | 9/2010 | Perry | |
| 7,850,635 B2 | 12/2010 | Polaschegg | |
| 7,857,976 B2 | 12/2010 | Bissler | |
| 7,867,214 B2 | 1/2011 | Childers | |
| 7,896,831 B2 | 3/2011 | Sternby | |
| 7,922,686 B2 | 4/2011 | Childers | |
| 7,922,911 B2 | 4/2011 | Micheli | |
| 7,947,179 B2 | 5/2011 | Rosenbaum | |
| 7,955,291 B2 | 6/2011 | Sternby | |
| 7,967,022 B2 | 6/2011 | Grant | |
| 7,981,082 B2 | 7/2011 | Wang | |
| 8,000,000 B2 | 8/2011 | Greenberg | |
| 8,034,161 B2 | 10/2011 | Gura | |
| 8,070,709 B2 | 12/2011 | Childers | |
| 8,096,969 B2 | 1/2012 | Roberts | |
| 8,105,260 B2 | 1/2012 | Tonelli | |
| 8,183,046 B2 | 5/2012 | Lu | |
| 8,187,250 B2 | 5/2012 | Roberts | |
| 8,197,439 B2 | 6/2012 | Wang | |
| 8,202,241 B2 | 6/2012 | Karakama | |
| 8,246,826 B2 | 8/2012 | Wilt | |
| 8,273,049 B2 | 9/2012 | Demers | |
| 8,282,828 B2 | 10/2012 | Wallenas | |
| 8,292,594 B2 | 10/2012 | Tracey | |
| 8,313,642 B2 | 11/2012 | Yu | |
| 8,317,492 B2 | 11/2012 | Demers | |
| 8,357,113 B2 | 1/2013 | Childers | |
| 8,366,316 B2 | 2/2013 | Kamen | |
| 8,366,655 B2 | 2/2013 | Kamen | |
| 8,404,091 B2 | 3/2013 | Ding | |
| 8,409,441 B2 | 4/2013 | Wilt | |
| 8,496,809 B2 | 7/2013 | Roger | |
| 8,499,780 B2 | 8/2013 | Wilt | |
| 8,500,676 B2 | 8/2013 | Jansson | |
| 8,512,271 B2 | 8/2013 | Moissl | |
| 8,518,260 B2 | 8/2013 | Raimann | |
| 8,521,482 B2 | 8/2013 | Akonur | |
| 8,535,525 B2 | 9/2013 | Heyes | |
| 8,560,510 B2 | 10/2013 | Brueggerhoff | |
| 8,580,112 B2 | 11/2013 | Updyke | |
| 8,597,227 B2 | 12/2013 | Childers | |
| 8,696,626 B2 | 4/2014 | Kirsch | |
| 8,903,492 B2 | 12/2014 | Soykan | |
| 8,926,542 B2 | 1/2015 | Gerber | |
| 9,399,091 B2 * | 7/2016 | Sigg | A61M 1/16 |
| 2002/0042561 A1 | 4/2002 | Schulman | |
| 2002/0112609 A1 | 8/2002 | Wong | |
| 2003/0080059 A1 | 5/2003 | Peterson | |
| 2003/0097086 A1 | 5/2003 | Gura | |
| 2003/0105435 A1 | 6/2003 | Taylor | |
| 2003/0114787 A1 | 6/2003 | Gura | |
| 2004/0019312 A1 | 1/2004 | Childers | |
| 2004/0068219 A1 | 4/2004 | Summerton | |
| 2004/0099593 A1 | 5/2004 | DePaolis | |
| 2004/0147900 A1 | 7/2004 | Polaschegg | |
| 2004/0168969 A1 | 9/2004 | Sternby | |
| 2004/0215090 A1 | 10/2004 | Erkkila | |
| 2005/0065760 A1 | 3/2005 | Murtfeldt | |

(56) References Cited

U.S. PATENT DOCUMENTS

| | | |
|---|---|---|
| 2005/0113796 A1 | 5/2005 | Taylor |
| 2005/0126961 A1 | 6/2005 | Bissler |
| 2005/0131331 A1 | 6/2005 | Kelly |
| 2005/0126998 A1 | 7/2005 | Childers |
| 2005/0150832 A1 | 7/2005 | Tsukamoto |
| 2005/0234381 A1 | 10/2005 | Niemetz |
| 2005/0236330 A1 | 10/2005 | Nier |
| 2005/0274658 A1 | 12/2005 | Rosenbaum |
| 2006/0025661 A1 | 2/2006 | Sweeney |
| 2006/0217771 A1 | 2/2006 | Soykan |
| 2006/0058731 A1 | 3/2006 | Burnett |
| 2006/0195064 A1 | 8/2006 | Plahey |
| 2006/0226079 A1 | 10/2006 | Mori |
| 2006/0241709 A1 | 10/2006 | Soykan |
| 2006/0264894 A1 | 11/2006 | Moberg |
| 2007/0007208 A1 | 1/2007 | Brugger |
| 2007/0066928 A1 | 3/2007 | Lannoy |
| 2007/0073168 A1* | 3/2007 | Zhang ............... A61B 5/0816 600/483 |
| 2007/0138011 A1 | 6/2007 | Hofmann |
| 2007/0175827 A1 | 8/2007 | Wariar |
| 2007/0179431 A1 | 8/2007 | Roberts |
| 2007/0213653 A1 | 9/2007 | Childers |
| 2007/0215545 A1 | 9/2007 | Bissler |
| 2007/0255250 A1 | 11/2007 | Moberg |
| 2008/0006570 A1 | 1/2008 | Gura |
| 2008/0021337 A1 | 1/2008 | Li |
| 2008/0053905 A9 | 3/2008 | Brugger |
| 2008/0067132 A1 | 3/2008 | Ross |
| 2008/0093276 A1 | 4/2008 | Roger |
| 2008/0215247 A1 | 9/2008 | Tonelli |
| 2008/0253427 A1 | 10/2008 | Kamen |
| 2009/0020471 A1 | 1/2009 | Tsukamoto |
| 2009/0101577 A1 | 4/2009 | Fulkerson |
| 2009/0124963 A1 | 5/2009 | Hogard |
| 2009/0127193 A1 | 5/2009 | Updyke |
| 2009/0171261 A1 | 7/2009 | Sternby |
| 2009/0264776 A1 | 10/2009 | Vardy |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2009/0314063 A1 | 12/2009 | Sternby |
| 2010/0004588 A1 | 1/2010 | Yeh |
| 2010/0010429 A1 | 1/2010 | Childers |
| 2010/0042035 A1 | 2/2010 | Moissl |
| 2010/0076398 A1 | 3/2010 | Scheurer |
| 2010/0078381 A1 | 4/2010 | Merchant |
| 2010/0078387 A1 | 4/2010 | Wong |
| 2010/0084330 A1 | 4/2010 | Wong |
| 2010/0087771 A1 | 4/2010 | Karakama |
| 2010/0094158 A1 | 4/2010 | Solem |
| 2010/0113891 A1 | 5/2010 | Barrett |
| 2010/0114012 A1 | 5/2010 | Sandford |
| 2010/0137693 A1 | 6/2010 | Porras |
| 2010/0137782 A1 | 6/2010 | Jansson |
| 2010/0168546 A1 | 7/2010 | Kamath |
| 2010/0217180 A1 | 8/2010 | Akonur |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |
| 2010/0264086 A1 | 10/2010 | Noack |
| 2011/0017665 A1 | 1/2011 | Updyke |
| 2011/0048949 A1 | 3/2011 | Ding et al. |
| 2011/0066043 A1 | 3/2011 | Banet |
| 2011/0071465 A1 | 3/2011 | Wang |
| 2011/0077574 A1 | 3/2011 | Sigg |
| 2011/0079558 A1 | 4/2011 | Raimann |
| 2011/0087187 A1 | 4/2011 | Beck |
| 2011/0100909 A1 | 5/2011 | Stange |
| 2011/0106003 A1 | 5/2011 | Childers |
| 2011/0130666 A1 | 6/2011 | Dong |
| 2011/0144570 A1 | 6/2011 | Childers |
| 2011/0184340 A1 | 7/2011 | Tan |
| 2011/0208105 A1 | 8/2011 | Brandl |
| 2011/0272337 A1 | 11/2011 | Palmer |
| 2011/0301447 A1 | 12/2011 | Park |
| 2012/0016228 A1 | 1/2012 | Kroh |
| 2012/0083729 A1 | 4/2012 | Childers |
| 2012/0085707 A1 | 4/2012 | Beiriger |
| 2012/0115248 A1 | 5/2012 | Ansyln |
| 2012/0220528 A1 | 8/2012 | VanAntwerp |
| 2012/0258546 A1 | 10/2012 | Marran |
| 2012/0259276 A1 | 10/2012 | Childers |
| 2012/0273415 A1 | 11/2012 | Gerber |
| 2012/0273420 A1 | 11/2012 | Gerber |
| 2012/0277546 A1 | 11/2012 | Soykan |
| 2012/0277551 A1 | 11/2012 | Gerber |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2013/0037465 A1 | 2/2013 | Heyes |
| 2013/0062265 A1 | 3/2013 | Balschat |
| 2013/0193073 A1 | 8/2013 | Hogard |
| 2013/0199998 A1 | 8/2013 | Kelly |
| 2013/0211730 A1 | 8/2013 | Wolff |
| 2013/0213890 A1 | 8/2013 | Kelly |
| 2013/0228517 A1 | 9/2013 | Roger |
| 2013/0231607 A1 | 9/2013 | Roger |
| 2013/0248426 A1 | 9/2013 | Pouchoulin |
| 2013/0274642 A1 | 10/2013 | Soykan |
| 2013/0324915 A1 | 12/2013 | (Krensky)Britton |
| 2013/0330208 A1 | 12/2013 | Ly |
| 2013/0331774 A1 | 12/2013 | Farrell |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0217028 A1 | 8/2014 | Pudil |
| 2014/0217029 A1 | 8/2014 | Meyer |
| 2014/0217030 A1 | 8/2014 | Meyer |
| 2014/0220699 A1 | 8/2014 | Pudil |
| 2015/0032023 A1 | 1/2015 | Soykan |
| 2015/0080682 A1 | 3/2015 | Gerber |
| 2015/0088047 A1 | 3/2015 | Gerber |
| 2015/0144539 A1 | 5/2015 | Pudil |
| 2015/0250427 A1 | 9/2015 | Soykan |
| 2015/0352269 A1 | 12/2015 | Gerber |
| 2015/0367054 A1 | 12/2015 | Gerber |
| 2016/0206801 A1 | 7/2016 | Gerber |
| 2016/0331884 A1 | 11/2016 | Sigg |

FOREIGN PATENT DOCUMENTS

| | | |
|---|---|---|
| EP | 266795 A2 | 11/1987 |
| EP | 0272414 | 10/1991 |
| EP | 0330892 | 7/1994 |
| EP | 1124599 | 5/2000 |
| EP | 1175238 | 11/2000 |
| EP | 2308526 | 10/2003 |
| EP | 1364666 A1 | 11/2003 |
| EP | 1523347 | 1/2004 |
| EP | 1523350 | 1/2004 |
| EP | 0906768 B1 | 2/2004 |
| EP | 1691863 | 4/2005 |
| EP | 2116269 | 2/2008 |
| EP | 1450879 | 10/2008 |
| EP | 1514562 | 4/2009 |
| EP | 2219703 | 5/2009 |
| EP | 1592494 B1 | 6/2009 |
| EP | 2100553 A1 | 9/2009 |
| EP | 2398529 | 11/2010 |
| EP | 2575827 A2 | 12/2010 |
| EP | 2100553 | 8/2011 |
| EP | 2576453 A2 | 12/2011 |

(56) References Cited

FOREIGN PATENT DOCUMENTS

| | | |
|---|---|---|
| EP | 2701595 | 11/2012 |
| EP | 1345856 B1 | 3/2013 |
| EP | 2344220 B1 | 4/2013 |
| EP | 1351756 | 7/2013 |
| EP | 2190498 | 7/2013 |
| EP | 1582226 | 1/2016 |
| JP | 2002542900 | 12/2002 |
| JP | 2003235965 | 8/2003 |
| JP | 5099464 | 10/2012 |
| WO | 1995003839 | 2/1995 |
| WO | 9937342 | 7/1999 |
| WO | 0057935 | 10/2000 |
| WO | 200066197 A1 | 11/2000 |
| WO | 2000066197 | 11/2000 |
| WO | 200170307 A1 | 9/2001 |
| WO | 2001085295 A2 | 9/2001 |
| WO | 0185295 A2 | 11/2001 |
| WO | 1085295 | 11/2001 |
| WO | 2002013691 | 2/2002 |
| WO | 2003043677 A2 | 5/2003 |
| WO | 2003043680 | 5/2003 |
| WO | 2003051422 A2 | 6/2003 |
| WO | 2004008826 | 1/2004 |
| WO | 2004009156 | 1/2004 |
| WO | 2004009158 | 1/2004 |
| WO | 2004030716 A2 | 4/2004 |
| WO | 2004030717 A2 | 4/2004 |
| WO | 2004064616 A2 | 8/2004 |
| WO | 2005061026 | 7/2005 |
| WO | 2005123230 A2 | 12/2005 |
| WO | 2006011009 | 2/2006 |
| WO | 2006017446 | 2/2006 |
| WO | 2007038347 | 4/2007 |
| WO | 2007089855 A2 | 8/2007 |
| WO | 2008037410 | 4/2008 |
| WO | 2009026603 | 12/2008 |
| WO | 2009024566 | 2/2009 |
| WO | 2009026603 A1 | 3/2009 |
| WO | 2009061608 | 5/2009 |
| WO | 2009094184 | 7/2009 |
| WO | 2009157877 A1 | 12/2009 |
| WO | 2009157878 A1 | 12/2009 |
| WO | 2010024963 | 3/2010 |
| WO | 2010028860 | 3/2010 |
| WO | 2010028860 A1 | 3/2010 |
| WO | 2010033314 | 3/2010 |
| WO | 2010033699 | 3/2010 |
| WO | 2010077851 | 7/2010 |
| WO | 2010096659 | 10/2010 |
| WO | 2010121820 | 10/2010 |
| WO | 2011025705 A1 | 3/2011 |
| WO | 2011026645 | 3/2011 |
| WO | 2011137693 | 11/2011 |
| WO | 2012042323 | 4/2012 |
| WO | 2012050781 | 4/2012 |
| WO | 2012051996 | 4/2012 |
| WO | 2012073420 | 7/2012 |
| WO | 2701580 | 11/2012 |
| WO | 2012148781 | 11/2012 |
| WO | 2012148786 | 11/2012 |
| WO | 2012148787 A1 | 11/2012 |
| WO | 2012148789 | 11/2012 |
| WO | 2012162515 A2 | 11/2012 |
| WO | 2012172398 | 12/2012 |
| WO | 2013019179 A1 | 2/2013 |
| WO | 2013019994 A2 | 2/2013 |
| WO | 2013025844 | 2/2013 |
| WO | 2013028809 A3 | 2/2013 |
| WO | 2013101292 | 7/2013 |
| WO | 2013103607 A1 | 7/2013 |
| WO | 2013103906 | 7/2013 |
| WO | 2013110906 | 8/2013 |
| WO | 2013110919 | 8/2013 |
| WO | 2013114063 A1 | 8/2013 |
| WO | 2013121162 A1 | 8/2013 |
| WO | 2013140346 | 9/2013 |
| WO | 2013141896 | 9/2013 |
| WO | 2013101292 A3 | 10/2013 |
| WO | 2701596 | 3/2014 |
| WO | 14066254 | 5/2014 |
| WO | 14066255 | 5/2014 |
| WO | 14077082 | 5/2014 |
| WO | 2014121162 | 8/2014 |
| WO | 2014121163 | 8/2014 |
| WO | 2014121167 | 8/2014 |
| WO | 2014121169 | 8/2014 |

OTHER PUBLICATIONS

Weissman, S., et al., "Hydroxyurea-induced hepatitis in human immunodeficiency virus-positive patients." Clin. Infec. Dis, (Jul. 29, 1999): 223-224.

Wheaton, et al., Dowex Ion Exchange Resins—Fundamentals of Ion Exchange; Jun. 2000, pp. 1-9. http://www.dow.com/scripts/litorder.asp?filepath=liquidseps/pdfs/noreg/177-01837.pdf.

Maclean, et, al., Effects of hindlimb contraction on pressor and muscle interstitial metabolite responses in the cat, J. App. Physiol., 1998, 1583-1592, 85(4).

Overgaard, et. al., Activity-induced recovery of excitability in K+-depressed rat soieus muscle, Am. J. P.

Overgaard. et. al., Relations between excitability and contractility in rate soleus'muscle: role of the NA+-K+ pump and NA+-K-S gradients. Journal of Physiology, 1999, 215-225, 518(1).

Roberts M, The regenerative dialysis (REDY) sorbent system. Nephrology, 1998, 275-278:4.

Ronco et al. 2008, 'Cardiorenal Syndrome,' Journal American College Cardiology, 52:1527-1539, Abstract.

Siegenthaler, et al., Pulmonary fluid status monitoring with intrathoracic impedance, Journal of Clinical Monitoring and Computing, 24:449-451, 2010.

U.S. Appl. No. 13/424,479.
U.S. Appl. No. 61/480,528.
U.S. Appl. No. 61/480,535.
U.S. Appl. No. 61/480,539.
U.S. Appl. No. 61/480,541.

Wang, Fundamentals of intrathoracic impedance monitoring in heart failure, Am. J. Cardiology, 2007, 3G-10G: Suppl.

PCT/US2014/067650 International Search Report Written Opinion dated Mar. 9, 2015.

Brynda, et. al., The detection of toman 2-microglcbuiin by grating coupler immunosensor with three dimensional antibody networks. Biosensors & Bioelectronics, 1999, 363-368, 14(4).

Hemametrics, Crit-Line Hematocrit Accuracy, 2003, 1-5, vol. 1, Tech Note No. 11 (Rev. D).

Lima, et. al., An electrochemical sensor based on nanostructure hollsndite-type manganese oxide for detection of potassium ion, Sensors, 2009, 6613-8625, 9.

Nedelkov, et. al., Design of buffer exchange surfaces and sensor chips for biosensor chip mass spectrometry, Proteomics, 2002, 441-446, 2(4).

PCT/US/2012/034327, International Search Report, dated Aug. 13, 2013.

PCT/US/2012/034329, International Search Report, dated Dec. 3, 2012.

PCT/US2012/034331, International Search Report, dated Jul. 9, 2012.

PCT/US2012/034332, International Search Report, dated Jul. 5, 2012.

PCT/US2012/034334, International Search Report, dated Jul. 6, 2012.

PCT/US2012/034335, International Search Report, dated Sep. 5, 2012.

U.S. Appl. No. 13/368,225.

Redfield, et. al, Restoration of renal response to atria! natriuretic factor in experimental low-output heat failure, Am. J. Physiol., 1989, R917-923:257.

(56) References Cited

OTHER PUBLICATIONS

Rogoza, et. al., Validation of A&D UA-767 device for the self-measurement of blood pressure, Blood Pressure Monitoring, 2000, 227-231, 5(4).
Secemsky, et. al, High prevalence of cardiac autonomic dysfunction and T-wave alternans in dialysis patients. Heart Rhythm, Apr. 2011, 592-598 : vol. 8, No. 4.
Wei, et. al., Fullerene-cryptand coated piezoelectric crystal urea sensor based on urease, Analytica Chimica Acta, 2001,77-85:437.
Zhong, et. al., Miniature urea sensor based on H(+)-ion sensitive field effect transistor and its application in clinical analysis, Chin. J. Biotechnol., 1992, 57-65. 8(1).
Leifer et al., 'A Study on the Temperature Variation of Rise Velocity for Large Clean Bubbles,' J. Atmospheric & Oceanic Tech., vol. 17, pp. 1392-1402.
Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.
Talaia, 'Terminal Velocity of a Bubble Rise in a Liquid Column,' World Acad. of Sci., Engineering & Tech., vol. 28, pp. 264-268.
The FHN Trial Group. In-Center. Hemodialysis Six Times per Week versus Three Times per Week, New England Journal of Medicine, 2010 Abstract.
U.S. Appl. No. 13/757,693, filed Feb. 1, 2013.
PCT/US2014/014357 International Search Report and Written Opinion.
Coast, et al. 1990, An approach to Cardiac Arrhythmia analysis Using Hidden Markov Models, IEEE Transactions on Biomedical Engineering. 1990, 37(9):826-835.
PCT/US2012/034330, International Preliminary Report on Patentability, dated Oct. 29, 2013.
PCT Application, PCT/US20013/020404, filed Jan. 4, 2013.
PCT/US2012/034333, International Preliminary Report on Patentability, dated Oct. 29, 2013.
PCT/US2012/034333, International Search Report, dated Aug. 29, 2013.
Gambro AK 96 Dialysis Machine Operator's Manual, Dec. 2012.
PCT/US2012/034335, International Preliminary Report on Patentability, dated Nov. 7, 2013.
PCT/US2012/034329, International Preliminary Report on Patentability, dated Oct. 29, 2013.
U.S. Appl. No. 13/837,287, filed Mar. 15, 2013.
Bleyer, et. al., Sudden and cardiac death rated in hemodialysis patients, Kidney International. 1999, 1553-1559: 55.
U.S. Appl. No. 13/424,517 IDS, filed Aug. 2, 2012.
U.S. Appl. No. 13/424,517, IDS filed Dec. 2, 2013.
PCT/US2012/034332, Internatonal Preliminary Report on Patentability, dated Oct. 29, 2013.
PCT/US2012/034303, Internationa Search Report, dated Jul. 6, 2013.
PCT/US2012/034327, International Preliminary Report on Patentability, dated Oct. 29, 2013.
Zoccali, Pulmonary Congestion Predicts Cardiac Events and Mortality in ESRD, Clinical Epidemiology, J. Am Soc Nephrol 24:639-646, 2013.
Velasco, Optimal Fluid Control can Normalize Cardiovascular Risk Markers and Limit Left Ventricular Hypertrophy in Thrice Weekly Dialysis Patients, Hemodialysis Intenational, 16:465-472, 2012.
Whitman, CKD and Sudden Cardiac Death: Epidemiology, Mechanisms, and Therapeutic Approaches, J Am Soc Nephrol, 23:1929-1939, 2012.
Hall, Hospitalization for Congestive Heart Failure: United States, 2000-2010, NCHS Data Brief, No. 108, Oct. 2012.
Albert, Fluid Management Strategies in Heart Failure, Critical Care Nurse, 32:20-32, 2012.
PCT/US2014/065201 International Search Report dated May 26, 2015.
John Wm Agar: "Review: Understanding sorbent dialysis systems," Nephrology, vol. 15, No. 4, Jun. 1, 2010, pp. 406-411.
Office Action in Chinese Application No. 201510511657.9 dated Dec. 28, 2016.
U.S. Appl. No. 61/480,530.
U.S. Appl. No. 61/480,532.
U.S. Appl. No. 61/480,544.
U.S. Appl. No. 13/424,533.
U.S. Appl. No. 13/424,467.
U.S. Appl. No. 13/424,429.
U.S. Appl. No. 13/424,454.
U.S. Appl. No. 13/424,490.
U.S. Appl. No. 13/424,517.
U.S. Appl. No. 13/424,525.
U.S. Appl. No. 13/757,794, filed Feb. 2, 2013.
U.S. Appl. No. 13/757,722, filed Feb. 1, 2013.
U.S. Appl. No. 13/757,792, filed Feb. 2, 2013.
U.S. Appl. No. 13/791,755, filed Mar. 8, 2013.
U.S. Appl. No. 13/836,973, filed Mar. 15, 2013.
U.S. Appl. No. 14/259,655, filed Apr. 23, 2014.
U.S. Appl. No. 14/259,589, filed Apr. 23, 2014.
U.S. Appl. No. 13/757,794, filed Feb. 2, 2012.
Weiner, et. al., Article: Cardiac Function and Cardiovascular Disease in Chronic Kidney Disease, Book: Primer on Kidney Diseases (Author: Greenberg, et al), 2009,499-505, 5th Ed., Saunders Elsevier, Philadelphia, PA.
Office Action in Chinese Application No. 201510511657.9 dated May 10, 2017.
Office Action in European Application No. EP 12717021.5 dated Feb. 3, 2017.

\* cited by examiner

SYSTEM AND METHOD TO REGULATE ULTRAFILTRATION

CROSS-REFERENCE TO RELATED APPLICATIONS

This application is a divisional of allowed U.S. application Ser. No. 12/571,127, filed Sep. 30, 2009, which is hereby incorporated by reference in its entirety to the extent that it does not conflict with the disclosure presented herein.

TECHNICAL FIELD

The disclosure relates generally to implantable medical devices and, in particular, to an implantable medical device (IMD) system and associated method for regulating ultrafiltration therapy.

BACKGROUND

In the early stages of heart failure, compensatory mechanisms occur in response to the heart's inability to pump a sufficient amount of blood. One compensatory response is an increase in filling pressure of the heart. The increased filling pressure increases the volume of blood in the heart, allowing the heart to eject a larger volume of blood on each heart beat. Increased filling pressure and other compensatory mechanisms can initially occur without overt heart failure symptoms.

The mechanisms that initially compensate for insufficient cardiac output, however, lead to heart failure decompensation as the heart continues to weaken. The weakened heart can no longer pump effectively causing increased filling pressure to lead to chest congestion (thoracic edema) and heart dilation, which further compromises the heart's pumping function. The patient begins the "vicious cycle" of heart failure which generally leads to hospitalization.

Typically, therapy for a patient hospitalized for acute decompensated heart failure includes early introduction of intravenous infusion of diuretics or vasodilators to clear excess fluid retained by the patient. A new therapy being introduced to remove excess fluid volume from patients with congestive heart failure and/or renal dysfunction is ultrafiltration. Ultrafiltration involves filtering a patient's blood to remove excess fluid then returning the filtered blood back to the patient. Ultrafiltration methods currently in use require manual control of the ultrafiltration unit. A challenge faced in delivering ultrafiltration therapy is knowing when and how much fluid to remove and the rate at which to remove fluid. Removing fluid too quickly may deplete intravascular fluid volume at a rate faster than edematous fluid can be reabsorbed from the tissues. Removing fluid too slowly may allow symptoms and the adverse affects of high filling pressures to persist longer than necessary. If the total fluid volume removed is insufficient, patient symptoms may not be fully alleviated, or alleviated symptoms may return quickly. Overdiuresis can occur if too much fluid is removed. Overdiuresis may require fluid to be administered to the patient to increase the patient's fluid volume status. Removing and adding fluid can pose additional burden on the kidneys, which may already be compromised due to renal insufficiency. A need remains, therefore, for a system and method for use in regulating ultrafiltration therapy.

DETAILED DESCRIPTION

In the following description, references are made to illustrative embodiments. It is understood that other embodiments may be utilized without departing from the scope of the invention. For purposes of clarity, the same reference numbers are used in the drawings to identify similar elements.

As used herein, the term "controller" refers to an application specific integrated circuit (ASIC), an electronic circuit, a processor (shared, dedicated, or group) and memory that execute one or more software or firmware programs, a combinational logic circuit, or other suitable components that provide the described functionality.

Figure 1:
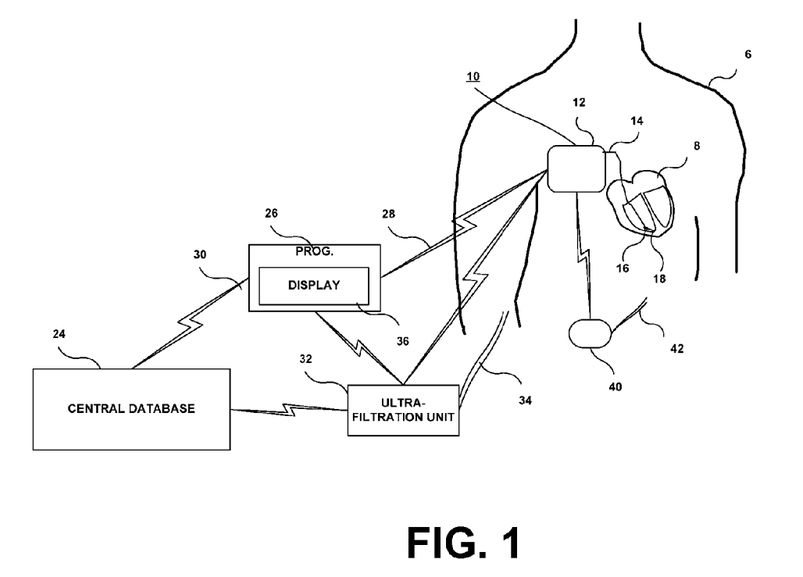
FIG. 1 is a schematic diagram of an implantable medical device (IMD) coupled to a lead positioned within a heart in a patient's body.

FIG. 1 is a schematic diagram of an implantable medical device (IMD) 10 coupled to a lead 14 positioned within a heart 8 in a patient's body 6. IMD 10 is capable of monitoring at least one physiological signal from which variables useful in monitoring a patient's fluid status can be derived. IMD 10 may or may not be provided with therapy delivery capabilities. IMD 10 may correspond to a variety of implantable medical devices including a cardiac pacemaker, implantable cardioverter defibrillator, implantable hemodynamic monitor, a drug pump, a neurostimulator or the like. Accordingly, IMD 10 may be coupled to additional leads and/or catheters operatively positioned relative to the patient's heart 8 or other body tissues for deploying stimulating/sensing electrodes, other physiological sensors, and/or drug delivery ports. While lead 14 is shown terminated within the right ventricle of the patient's heart, it is recognized that lead 14 may be configured as a transvenous lead that extends into other heart chambers or blood vessels for positioning electrodes and/or physiological sensors in a desired location.

In one embodiment, IMD 10 corresponds to an implantable hemodynamic monitor capable of sensing and recording ECG signals, intracardiac right ventricular pressure signals, and transthoracic impedance signals. IMD 10 stores the sensed signals and further derives fluid status measurements from the sensed signals for monitoring the fluid volume status of the patient. ECG signals are sensed using one or more electrodes 18 carried by lead 14 or using alternative electrodes (not shown) incorporated on the housing 12 of IMD 10. Housing 12 encloses circuitry (not shown in FIG. 1) included in IMD 10 for controlling and performing device functions and processing sensed signals.

An electrode 18 carried by lead 14 is used with the IMD housing 12 for measuring a transthoracic impedance for use in monitoring intrathoracic fluid status. As used herein, "transthoracic" impedance refers to any impedance measurement across a portion of the thorax, including across a portion of the heart, lungs and/or pulmonary vascular bed. In alternative embodiments, one or more lead-based electrodes and/or one or more subcutaneously placed electrodes, incorporated on IMD housing 12 or carried by a subcutaneously extending lead, may be used to measure transthoracic impedance across a portion of the thoracic cavity, heart and/or lungs for use in deriving a variable useful in monitoring fluid status.

Transthoracic electrical impedance decreases as the fluid in the chest increases. Transthoracic impedance decreases with heart failure decompensation as fluid accumulates in the chest and the heart and blood vessels dilate due to elevated right heart filling pressures and insufficient cardiac ejection. As such, transthoracic impedance measurements may be used in deriving a fluid status measurement useful in controlling ultrafiltration therapy administered to a patient.

As used herein, a "fluid status measurement" is a measurement or index derived from a physiological sensor signal and is correlated to the blood volume of the patient or edemic state of the patient. As such a worsening fluid status measurement is a measurement that corresponds to increased fluid retention by the patient corresponding to hypervolemia and/or edema. A hypervolemic volume state of the patient occurs when the volume status exceeds the optivolemic state and corresponds to a fluid status measurement that crosses an optivolemic level of the fluid status measurement, which may be an increasing or decreasing change in the fluid status measurement depending on the particular measurement being used. For example, intraventricular pressure would increase with fluid overload and would decrease in a state of overdiuresis or hypovolemia. A transthroracic impedance would decrease with fluid overload and increase with overdiruesis or hypovolemia. Other fluid status measurements may be derived from an oxygen sensor or a blood chemistry sensor measuring, for example, blood urea nitrogen, serum creatinine, serum electrolytes including calcium and magnesium, blood glucose, or thyroid stimulating hormone, or any combination of the foregoing measurements.

Lead 14 is further provided with a pressure sensor 16. Pressure sensor 16 is used for monitoring pressure within the right ventricle (RV) for use in deriving pressure-related fluid status measurements. The RV pressure signal can be used directly or used to determine an estimated pulmonary artery diastolic (ePAD), pressure which increases during heart failure decompensation. While ePAD pressure is one useful variable that can be derived from a RV pressure signal, numerous other pressure-related variables may be useful in monitoring a fluid status. Furthermore, pressure signals obtained at other locations in the heart or vasculature may be used for deriving a fluid status measurement.

Any blood pressure measurement acquired at any measurement site that is correlated to cardiac filling pressure may be used since increased cardiac filling pressure reflects a hypervolemic state and leads to pulmonary edema. Among the pressure measurements that may be used as a measure of cardiac filling pressure, i.e. to derive a fluid status measurement, are left ventricular end diastolic pressure, left atrial pressure, pulmonary venous pressure, pulmonary arterial diastolic pressure, right ventricular ePAD, right ventricular diastolic pressure, right atrial pressure, and central venous pressure. While the above listed measurements are all intravascular measurements made within the thorax (intrathoracic), it is also understood that other extrathoracic venous pressure measurements, such as hepatic venous pressure or jugular venous pressure, could also be used to indicate the patient's volume status for the purposes of controlling ultrafiltration.

IMD 10 is capable of bidirectional communication with an external device 26 via bidirectional telemetry link 28. Device 26 may be embodied as a programmer, typically located in a hospital or clinic, used to program the operating mode and various operational variables of IMD 10 and interrogate IMD 10 to retrieve data stored by IMD 10. Device 26 may alternatively be embodied as a home monitor used to retrieve data from the IMD 10 and may be used to program IMD 10 but may have limited programming functionality as compared to a hospital or clinic programmer. Data stored and retrieved from IMD 10 may include data related to IMD function determined through automated self-diagnostic tests as well as physiological data acquired by IMD 10 using pressure sensor 16 and electrode(s) 18.

External device 26 is further shown in communication with a central database 24 via communication link 30, which may be a wireless or hardwired link. Programming data and interrogation data may be transmitted via link 30. Central database 24 may be a centralized computer, web-based or other networked database used by a clinician for remote monitoring and management of patient 6. It is recognized that other external devices, such as other physiological monitoring devices or other types of programming devices, may be used in conjunction with IMD 10 and incorporate portions of the methods described herein.

An ultrafiltration unit 32 is coupled to the patient 6 via catheters 34 for removing excess fluid from the patient. The ultrafiltration unit 32 passes the patient's blood through a filter to remove fluid then returns the blood, with fluid removed, to the patient 6. In some embodiments, ultrafiltration unit 32 is enabled for telemetric communication with IMD 10, programmer or monitor 26 and/or central database 24. Ultrafiltration unit 32 may receive data, such as ultrafiltration control parameters, fluid status data for setting delivery control parameters, or notifications relating to the patient's fluid status. In this way, automated or semi-automated control of ultrafiltration therapy may be achieved using fluid status measurements obtained by IMD 10.

In other embodiments, ultrafiltration unit 32 is manually adjusted in response to fluid status measurements and notifications provided by IMD 10, which may be transmitted for viewing on an external display 36 by a nurse or clinician, or, in the case of home ultrafiltration, by the patient. Display 36 is shown implemented on programmer 26 but may alternatively or additionally be associated with central database 24. When ultrafiltration unit 32 is enabled for communication with IMD 10, programmer 26 or central database 24, ultrafiltration unit 32 may include a display (not shown) for displaying data received from the IMD system relating to the patient's fluid status. For example, fluid status measurements and/or recommended ultrafiltration control parameters may be received and stored on display 36 or another display incorporated in ultrafiltration unit 32. The remote transmission of fluid status data to a central database 24 so that it can be reviewed by an expert clinician allows the clinician to remotely set a range of ultrafiltration control parameters allowed to be used by the ultrafiltration unit 32.

Ultrafiltration unit 32 is an external unit that may be located in a hospital or clinic, a portable unit in a patient's home, or a wearable unit used by the patient in or away from a hospital or clinic. In other embodiments, an implantable ultrafiltration unit 40 may be used to deliver the ultrafiltration therapy. The implantable unit 40, like the external unit 32, would be coupled to the patient's vasculature using catheters 42 for receiving a volume of the patient's blood, filtering the blood to remove fluid, then returning the filtered blood back to the patient's vasculature system.

The implantable ultrafiltration unit 40 may be in wireless communication with IMD 10 for receiving data relating to the patient's fluid status. The fluid status measurements received from IMD 10 would be used by a controller in IMD 10 or in the ultrafiltration unit 40 for establishing ultrafiltration control parameters used by ultrafiltration unit 40. Ultrafiltration unit 40 may alternatively be configured for wireless communication with an external programmer, such as programmer 26 or another dedicated programmer, or central database 24. The external programmer or central database is provided with a controller for establishing ultrafiltration control parameters using the fluid status measurements obtained by IMD 10. The external programmer or central database either displays the recommended control parameters or transmits the control parameters to the implantable unit 40. Ultrafiltration unit 40 may then be programmed manually or automatically by an external programmer using control parameters established based on fluid status measurements from IMD 10. It is understood that additional communication links would be provided as needed between implantable unit 40 and external components 26 and 24 and are not shown explicitly in FIG. 1 for the sake of clarity.

In still other embodiments, it is contemplated to include a physiological sensor in, or coupled to, implantable ultrafiltration unit 40 for sensing a signal that can be used to compute a fluid status measurement. A controller in the ultrafiltration unit establishes ultrafiltration control parameters used for controlling ultrafiltration therapy in a closed loop manner within the implanted unit 40.

Various methods described herein for determining the fluid status of a patient using one or more physiological signals sensed by an implantable sensor, establishing ultrafiltration control parameters based on the physiological signals, and setting the control parameters in the ultrafiltration unit 32 or 40 may be implemented in one or more of the IMD system components shown in FIG. 1, namely IMD 10, external device 26, central database 24, and ultrafiltration unit 32 or 40. The described functionality may include any combination of hardware, firmware and/or software.

Figure 2:
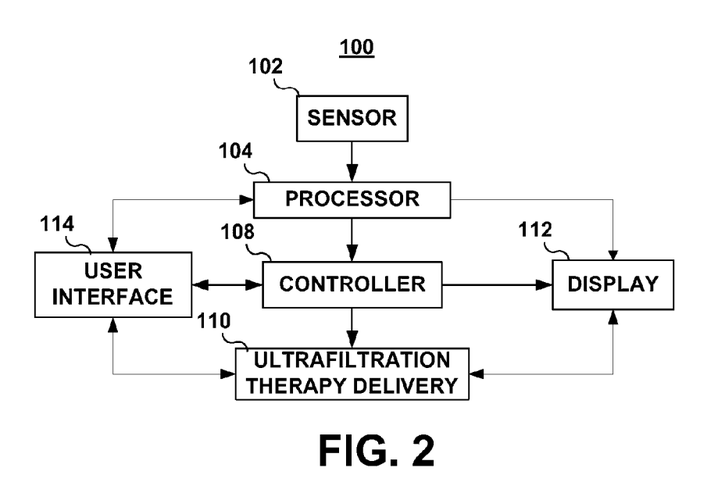
FIG. 2 is a functional block diagram of a medical device system including at least an implantable physiological sensor and an ultrafiltration unit.

FIG. 2 is a functional block diagram of a medical device system 100 including at least an implantable sensor for sensing physiological signals and an ultrafiltration unit for delivering ultrafiltration therapy. Physiological sensor 102 provides signals to a processor 104 which computes a fluid status measurement using the sensed signals. A controller 108 receives the computed fluid status measurements and determines control parameters for ultrafiltration therapy delivery 110. Control parameters may be set or adjusted automatically to control ultrafiltration therapy delivery 110. To facilitate manual adjustment of control parameters, a user interface 114 and display 112 is provided to display data relating to fluid status measurements and/or established control parameters and allow a user to enter commands or set control parameters accordingly. The user interface 114 and the display 112 may be integrated in a graphical user interface and may be a single interface used with a controller 108 or with ultrafiltration delivery 110. Display 112 may also be used to display notifications to a patient or clinician to indicate a need for ultrafiltration therapy or a need to adjust or terminate ultrafiltration.

In various embodiments, controller 108 may be implemented in the ultrafiltration unit, in the IMD, in a central database, or in an external programmer or home monitor or across any of these components. The controller 108 is adapted to receive fluid status measurement data and establish ultrafiltration control parameters in response to the data.

The controller 108 may or may not be adapted to automatically set established control parameters in the ultrafiltration unit. User intervention may be required in transferring fluid status measurement data to the controller and/or transferring established control parameters to the ultrafiltration therapy delivery 110 to set the control parameters and enable or disable ultrafiltration.

The functionality shown in FIG. 2 can be implemented in a single device, such as within an implantable ultrafiltration unit 40, including a physiological sensor and processing and control circuitry, or distributed across the various system components shown in FIG. 1, in which case it is understood that necessary communication modules are incorporated for transmitting data between system components as needed automatically or with user intervention.

Figure 3:
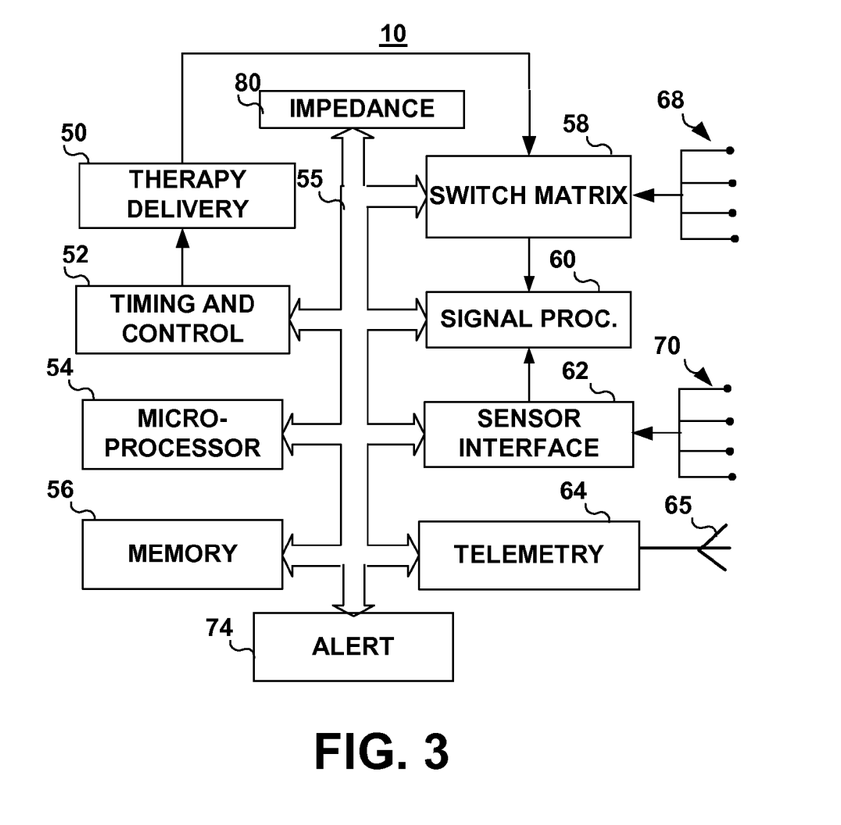
FIG. 3 is a functional block diagram of one embodiment of IMD.

FIG. 3 is a functional block diagram of one embodiment of IMD 10. IMD 10 generally includes timing and control circuitry 52 and a control unit that may employ microprocessor 54 or a digital state machine for timing sensing and therapy delivery functions (when present) in accordance with a programmed operating mode. Microprocessor 54 and associated memory 56 are coupled to the various components of IMD 10 via a data/address bus 55.

IMD 10 may include therapy delivery module 50 for delivering a therapy in response to determining a need for therapy, e.g., based on sensed physiological signals. Therapy delivery module 50 may provide drug delivery therapies or electrical stimulation therapies, such as cardiac pacing or anti-arrhythmia therapies. In some embodiments, IMD 10 may include ultrafiltration therapy capabilities and would then be coupled to catheters for receiving and pumping blood across a filter and returning blood to the patient's vasculature. Therapies are delivered by module 50 under the control of timing and control circuitry 52.

Therapy delivery module 50 may be coupled to two or more electrodes 68 via an optional switch matrix 58. Switch matrix 58 may be used for selecting which electrodes and corresponding polarities are used for delivering electrical stimulation pulses. Electrodes 68 may correspond to any electrodes incorporated in IMD housing 12 or other lead-based electrodes, including electrode(s) 18 carried by lead 14 (shown in FIG. 1).

As discussed above, IMD 10 may be configured to measure impedance signals for deriving a fluid status measurement. As such, selected electrodes 68 are coupled to impedance measuring module 80 for providing an impedance measurement drive signal along an excitation path. The voltage is then measured across the measuring electrodes allowing the impedance across the measurement path to be computed from the known drive signal and the measured voltage. Impedance measurement methods and associated apparatus are generally disclosed in PCT Publication WO 2008/014078 (Stylos), incorporated herein by reference in its entirety.

IMD 10 is additionally coupled to one or more sensors 70 used to monitor physiological signals. Physiological sensors 70 include pressure sensor 16 as shown in FIG. 1 and may further include sensors responsive to motion, flow, blood chemistry (including but not limited to blood urea nitrogen, serum creatinine, serum electrolytes including calcium and magnesium, blood glucose, and thyroid stimulating hormone), patient activity, patient posture, oxygen, temperature or other physiological sensors used in conjunction with implantable medical devices. Physiological sensors may be carried by leads extending from IMD 10, incorporated in or on the IMD housing 12, or embodied as wireless sensors in telemetric communication with IMD 10.

Sensor signals are received by a sensor interface 62 which may provide initial amplification, filtering, rectification, or other signal conditioning. Sensor signals may then be provided to signal processing circuitry 60 for analog-to-digital conversion, averaging, integration, peak detection or other signal processing required for a particular application to derive desired signal features used to compute fluid status measurements. Microprocessor 54 receives the processed sensor signals for detecting physiological events or conditions. In particular, signals from pressure sensor 16 are processed by signal processor 60 and/or microprocessor 54 for deriving a fluid status measurement from a pressure signal.

A fluid status monitoring algorithm may be stored in memory 56 and executed by microprocessor 54 with input received from electrodes 68, physiological sensors 70, signal processor 60 and impedance measuring module 80. Microprocessor 54 in conjunction with memory 56 may operate as a control unit for executing software-implemented algorithms for monitoring fluid status using an impedance variable and/or a pressure variable derived by processor 60, impedance module 80, and/or by microprocessor 54 using sensed signals. The algorithms stored in memory 56 are retrieved by microprocessor 54 as needed. In alternative embodiments, functionality described herein may be implemented using dedicated hardware and/or firmware.

Fluid status data may be stored in memory 56 for use in diagnosing or monitoring the patient, determining the need for delivering a therapy under control of the operating system, or a separate ultrafiltration unit. Memory 56 may store a variety of programmed parameter values that are used by microprocessor 54 for determining the need for therapy and for establishing therapy control parameters. Memory 56 may also be used for storing data compiled from sensed physiological signals and/or relating to device operating history for telemetry out on receipt of a retrieval or interrogation instruction.

IMD 10 further includes telemetry circuitry 64 and antenna 65. Programming commands or data are transmitted during uplink or downlink telemetry between IMD telemetry circuitry 64 and external telemetry circuitry included in a programmer or monitoring unit such as programmer 26 as shown in FIG. 1.

Alert module 74 generates patient or clinician notifications in response to detecting various patient-related or device-related conditions. A notification may be an audible sound or a message transmitted via telemetry 64 to an external device. A notification may be generated by module 74 in response to fluid status measurements determined by IMD 10. In particular, a notification may be generated by IMD 10 when fluid status measurements monitored by IMD 10 indicate a need to start, stop or adjust ultrafiltration therapy.

Figure 4:
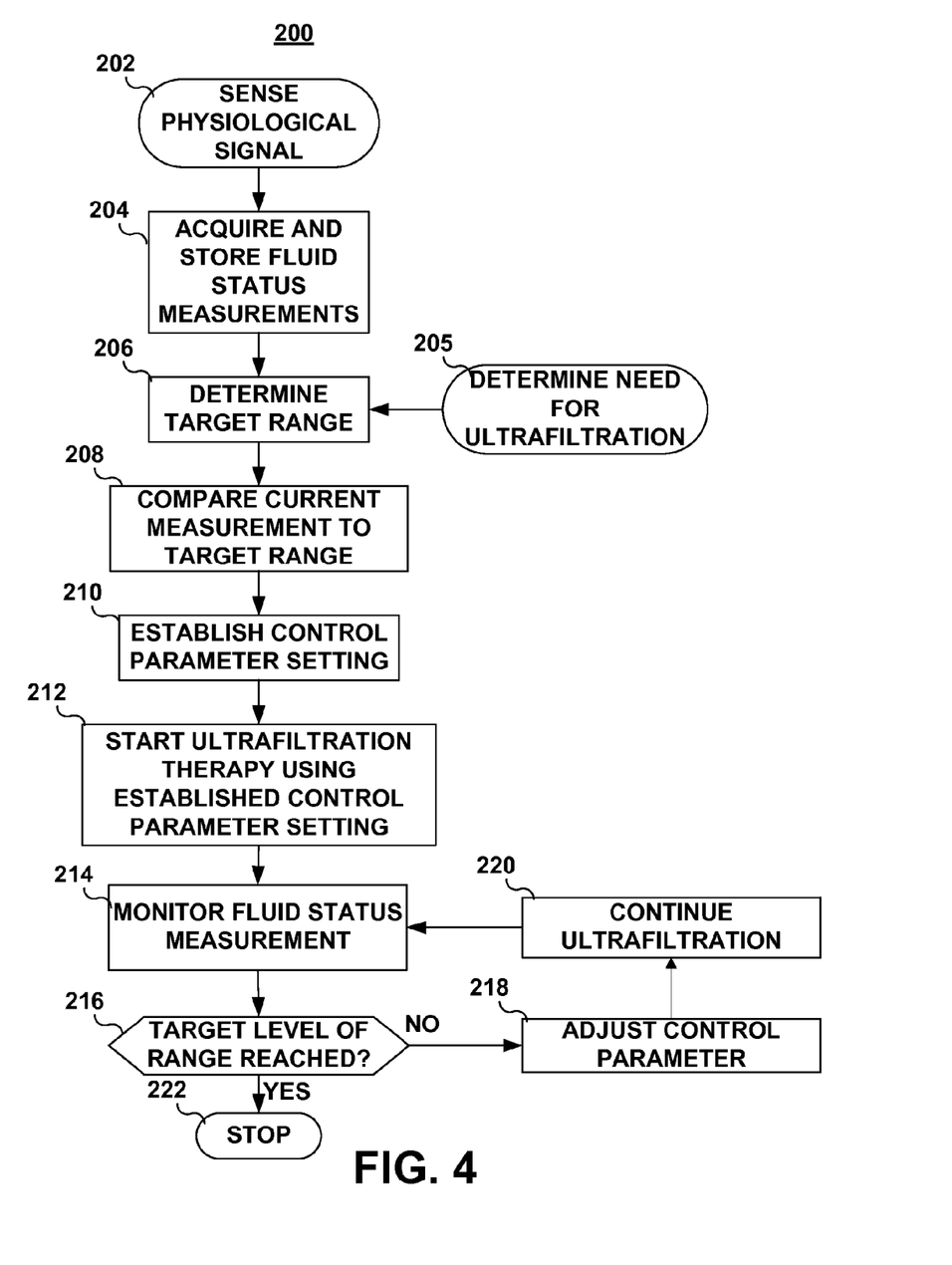
FIG. 4 is a flow chart of a method for regulating ultrafiltration therapy.

FIG. 4 is a flow chart 200 of one embodiment of a method for regulating ultrafiltration therapy. Flow chart 200 is intended to illustrate the functional operation of a medical device system, and should not be construed as reflective of a specific form of software or hardware necessary to practice the embodiments described herein. It is believed that the particular form of software will be determined primarily by the particular system architecture employed in the device system and by the particular sensing and therapy delivery methodologies employed by the system. Providing software to accomplish the described functionality in the context of any modern implantable medical device system, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 202, a physiological signal is sensed using an implantable physiological sensor for use in monitoring a patient's fluid status. The signal may be, without limitation, a blood pressure signal and/or an impedance signal as described previously. At block 204, fluid status measurements are computed and stored by the IMD, according to a programmed monitoring algorithm, using the sensed physiological signal(s). For example, hourly, daily, weekly or other periodic measurements may be acquired. The frequency of fluid status measurement acquisition will depend in part on the patient condition. For example, a patient suffering from renal dysfunction may be monitored at least daily to allow daily fluctuations in fluid status to be assessed. In a heart failure patient that experiences fluid overload infrequently, a weekly assessment may be adequate.

At block 206, a target range for the fluid status measurement is determined. The target range may be user-defined input by a clinician and stored in the IMD or a controller used to establish ultrafiltration control parameters. Alternatively, the target range is computed by the IMD or a controller using the patient's fluid status measurement history retrieved from IMD memory. The target range may be a pressure range, for example corresponding to an intracardiac blood pressure, ePAD pressure, central venous pressure, or other pressure measurement. In other embodiments, the target range may correspond to a transthoracic impedance measurement. In still other embodiments, the target range may be defined as a range of an index computed using a combination of two or more different fluid status measurements obtained by the IMD, such as any combination of an intracardiac pressure, a transthoracic impedance, blood chemistries, oxygen, flow or other physiologic sensor signals.

The target range may be computed using stored fluid status measurements by the IMD processor, by a processor included in an external programmer or home monitor, by a central database used for remote patient monitoring, or by a controller incorporated in the ultrafiltration unit or separately from the ultrafiltration unit for establishing ultrafiltration control parameters. The target range is generally associated with an optivolemic level or range of the fluid status measurement at which the patient is expected to be stable with reduced (or no) symptoms associated with fluid overload.

The target range may be determined and stored prospectively at block 206. Alternatively, the target range may be determined at the time that a need for ultrafiltration therapy is recognized as indicated at block 205. For example, if a patient is hospitalized for symptoms associated with fluid overload, a clinician may prescribe ultrafiltration therapy. A clinician may interrogate the IMD using an external programmer to retrieve fluid status measurements. The fluid status measurement trended data may then be used by a controller to compute a target range for the fluid status measurement to be achieved by the ultrafiltration therapy. As will be described further below, the target range may be used in other embodiments for determining the need for ultrafiltration therapy.

At block 208 the currently measured fluid status measurement is compared to the ultrafiltration target range by the controller. This comparison is used to establish an ultrafiltration control parameter setting at block 210. For example, the control parameter may be a flow rate at which blood flows through the ultrafiltration system. A flow rate setting may be established according to how far a current fluid status measurement is out of the target range. In other words, the flow rate is adjusted in proportion to a difference between the fluid status measurement and a boundary of the target range, which may be the nearest or furthest boundary of the target range. The difference between a fluid status measurement and a boundary of the target range can be referred to as a "control signal" in that this difference is used to establish ultrafiltration control parameters. Hierarchal levels of flow rate may be set based on hierarchal levels or percentiles of the fluid status measurement values relative to the target range, i.e. the "control signal". In one illustrative example, the flow rate may be set to a high, medium or low rate depending on whether the fluid status measurement exceeds a predetermined high threshold above (or below in the case of an impedance measurement) the target range (a high control signal), a medium threshold outside the target range (a moderate control signal), or a low threshold outside the target range (a low control signal).

The ultrafiltration therapy is started at block 212 using the established control parameter setting. It is recognized that one or more control parameters may be established and set based on a current fluid status measurement and target range. During the ultrafiltration therapy, the fluid status measurement is monitored by the IMD at block 214. Fluid status monitoring during ultrafiltration may be performed continuously or on a periodic basis such as every minute, every hour, or at another periodic interval which may be a programmable interval.

If a target level within the target range is reached at block 216, the ultrafiltration therapy is stopped at block 222. A target level may be any level within the target range including one of the target range boundaries. For example, the target level may be set to a target range boundary corresponding to a "best" fluid status, i.e. a lower boundary for a pressure-based measurement and an upper boundary for an impedance-based measurement, or another level within the target range corresponding to an optimal fluid status measurement. By performing ultrafiltration until a target level within the target range or a furthest boundary is reached rather than just until the fluid status measurement reaches the nearest target range boundary, the fluid status is more likely to remain within the target range longer and more optimal results can be expected.

If the target level has not been reached, as determined at block 216, the control parameter may be adjusted at block 218 based on a comparison of an updated fluid status measurement and the target range. For example, if the updated measurement obtained after starting ultrafiltration has dropped from exceeding a high threshold or percentile to a medium threshold or percentile, the ultrafiltration flow rate may be reduced from a high rate to a medium rate at block 218.

Ultrafiltration is continued at block 220 using the adjusted control parameter, and fluid status continues to be monitored at block 214. If the target range is reached at block 216 (i.e., a nearest boundary of the target range is reached) but a target level within the target range has not yet been reached, the ultrafiltration control parameter may be reduced to a lowest setting at block 218 until the target level is reached. As such, in one embodiment, the ultrafiltration therapy can be described as being delivered with a hysteresis where stopping the ultrafiltration therapy lags the fluid status measurement reaching a target range by the time it takes to reach a target level within the target range or until the fluid status measurement has remained within the target range for some minimum period of time.

In the illustrative embodiment described, the control parameter of flow rate has been described as having three hierarchical settings, low, medium and high, which would be adjusted based on hierarchical thresholds applied to a fluid status measurement. However it is recognized that any number of settings may be applied to a control parameter based on multiple threshold levels applied to the fluid status measurement. Furthermore, continuous smooth adjustment of flow rate is contemplated as the fluid status measurement continuously improves during the ultrafiltration therapy. In other words, as the fluid status measurement continuously trends toward the target range, the ultrafiltration flow rate may be continuously decreased, or decreased in small stepwise increments, as the fluid status measurement improves.

Figure 5:
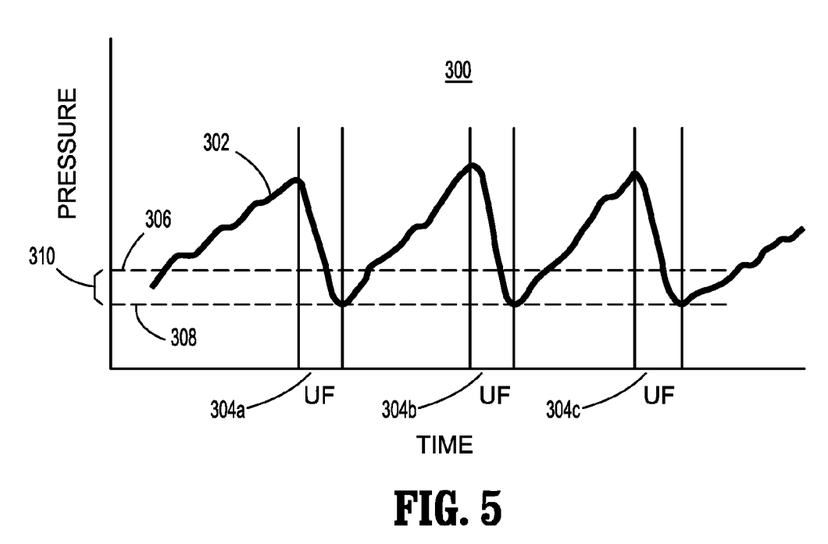
FIG. 5 is an illustrative time-based plot of a fluid status measurement as it might vary over the course of periodic ultrafiltration therapy sessions.

FIG. 5 is a time-based plot 300 illustrating a fluid status measurement as it might vary over the course of periodic ultrafiltration therapy sessions. A fluid status measurement 302 increases over time leading up to each periodic ultrafiltration therapy session 304a, 304b and 304c, also referred to collectively as sessions 304. Ultrafiltration therapy sessions 304 may be performed on a scheduled basis, for example, weekly, every three days, or another prescribed frequency. During the ultrafiltration therapy sessions 304, the fluid status measurement 302 is seen to decrease below an upper boundary 306 of a target range 310. Ultrafiltration is continued until the fluid status measurement 302 reaches a lower boundary 308 of the target range 310.

In this illustrative example, the fluid status measurement may correspond to, without limitation, right ventricular systolic pressure, right ventricular diastolic pressure, or ePAD pressure. Target ranges for these measurements will likely vary between patients but may be, for example, approximately 20 to 25 mmHg for right ventricular systolic pressure, approximately 2 to 3 mmHg for right ventricular diastolic pressure, and approximately 10 to 12 mmHg for ePAD pressure. Ultrafiltration therapy is indicated when the patient's fluid status measurement exceeds the target range and may be delivered until the measurement reaches the lower boundary of the target range.

Figure 6:
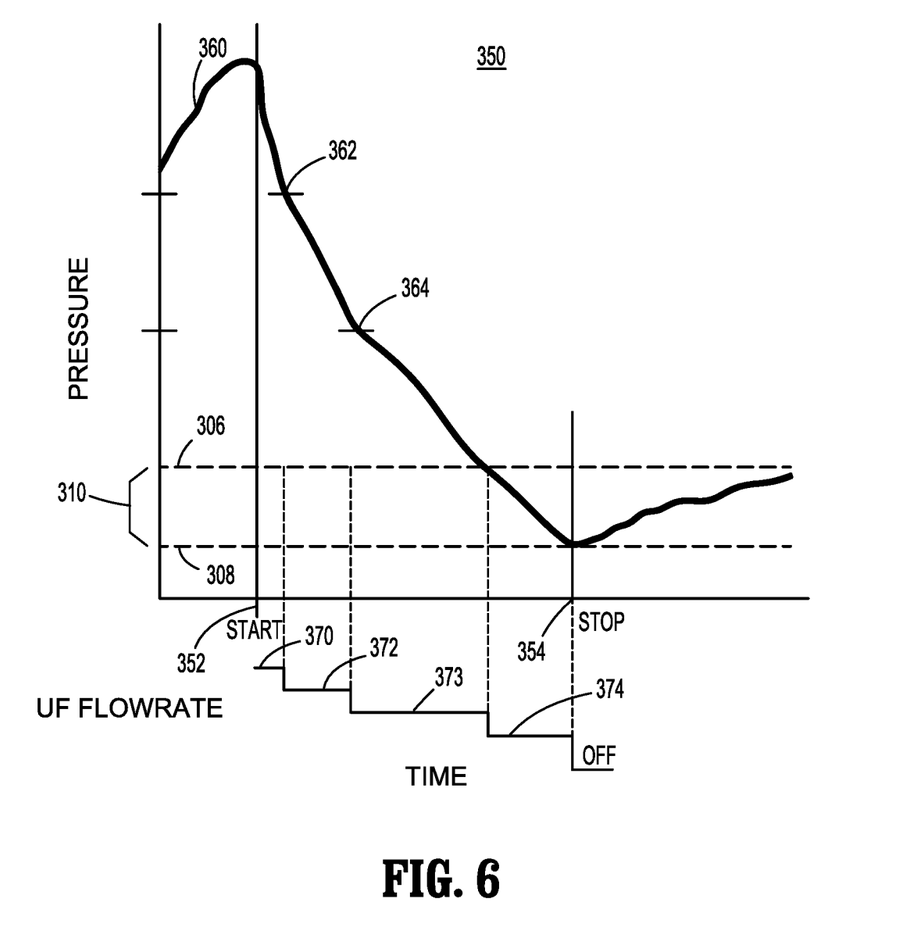
FIG. 6 is a time-based plot of a fluid status measurement during an ultrafiltration therapy session.

FIG. 6 is a time-based plot 350 illustrating changes that may occur in a fluid status measurement 360 during an ultrafiltration therapy session. In this example, the fluid status measurement 360 again corresponds to a pressure measurement though other fluid status measurements may be similarly monitored and may exhibit an increasing or decreasing trend as ultrafiltration therapy is delivered and the patient's fluid status improves.

The ultrafiltration therapy is started at 352 at an initially high flow rate 370. When the fluid status measurement 360 crosses a first threshold 362, defining the boundary of a high flow rate zone of the fluid status measurement 360, the ultrafiltration flow rate is adjusted to a relatively slower flow rate 372. Ultrafiltration is delivered at the flow rate 372 for an interval of time until the fluid status measurement 360 crosses a next, lower threshold 364. Upon reaching the next lower threshold 364, the flow rate is again decreased to a rate 373 until the fluid status measurement reaches the upper boundary 306 of target range 310. The upper boundary 306 is the nearest boundary to the initial fluid status measurement at the time ultrafiltration was started and the lower boundary 308 is the furthest boundary relative to the initial fluid status measurement.

Ultrafiltration continues at the lowest flow rate 374 after crossing the nearest (upper) boundary 306 until the furthest (lower) boundary 308 of target range 310 is reached. The changes in the flow rate are accompanied by a change in the slope of the fluid status measurement 360 as can be seen in FIG. 6. It is recognized that depending the fluid status measurement being used, a change in slope in the measurement may lag the change in the ultrafiltration control parameter. Methods described herein relate to adjusting an ultrafiltration flow rate however other ultrafiltration control parameters may be adjusted such as pressure across the ultrafiltration membrane.

Figure 7:
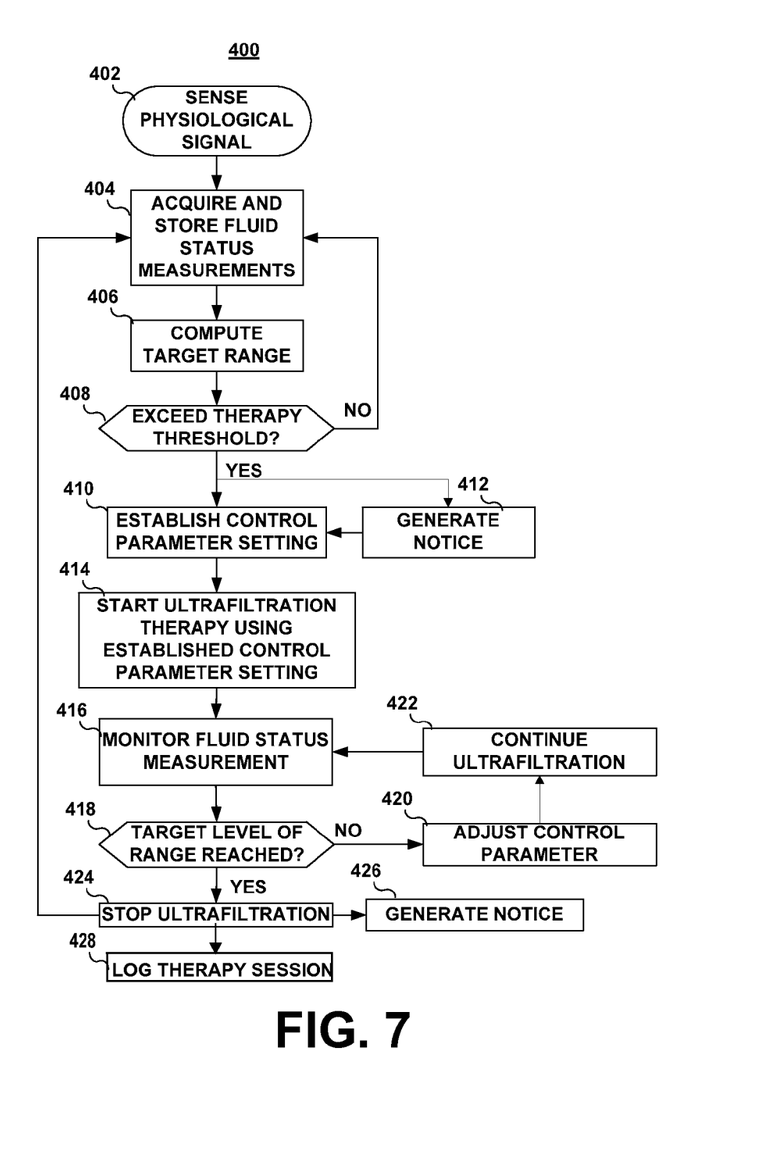
FIG. 7 is a flow chart of an alternative method for regulating ultrafiltration therapy.

FIG. 7 is a flow chart 400 of an alternative method for regulating ultrafiltration therapy. At block 402, a physiological signal is sensed and used to compute fluid status measurements acquired and stored at block 404. A target range corresponding to an optivolemic range of the fluid status measurement is computed automatically at block 406 using historical trends of the measurement. For example, a range in which a specified percentage of the fluid status measurements fall may be computed. To illustrate, a range in which approximately 80% of the fluid status measurements fall may be determined. In other words, a range in which the patient remains for a specified percentage of time may be identified. Alternatively, a distribution of the fluid status measurements may be determined and a percentile range of that distribution may be defined as the target range. In still other embodiments, a range may be defined relative to a mean or median value, averaged minimum or maximum measurements, or other feature of the historical data or any combination thereof In the absence of a historical trend in a given patient, e.g., soon after implant of the IMD, population-based values for an initial or default range of a given fluid status measurement may be used for setting a target range. If the IMD has acquired short term data, for example one day, rather than days or months of data, this short term data may be evaluated relative to the population based estimates for a target range to then determine initial control settings for the patient for an ultrafiltration episode. The ultrafiltration system could then "learn" the patient's target range as more, longer term data becomes available for that patient.

At block 408, the current fluid status measurement is compared to a therapy threshold. The threshold for indicating a need for ultrafiltration therapy may be a boundary of the target range or a value outside the target range. If the therapy threshold is not crossed, fluid status measurements continue to be acquired and stored. The target range may be automatically updated periodically using recent data.

If the therapy threshold is crossed, a notification may optionally be generated at block 412 by the IMD or other system component detecting the therapy threshold crossing. For example, a notification may be generated by the IMD and transmitted to an external programmer, home monitor or centralized database to notify the patient and/or a clinician or emergency responder of a need to initiate therapy or that the therapy is being initiated automatically. In some embodiments, the therapy will be initiated manually in response to an automatic determination of the need for therapy. In other embodiments, the therapy will be initiated automatically by a controller in response to the IMD (or other system component) detecting a therapy threshold crossing.

At block 410, the controller establishes a control parameter setting using the current value of the fluid status measurement. In some embodiments, the control parameter may be an on/off setting which enables or disables ultrafiltration automatically based on the fluid status measurement crossing a therapy threshold. If the ultrafiltration unit is embodied as an implantable device, ultrafiltration is automatically started in response to the therapy threshold crossing.

In other embodiments, other control parameters may be established, such as a flow rate, which may be established based on a valve setting or other mechanism that controls the rate of blood flowing through the ultrafiltration unit. For example, a valve may be controlled to be fully open (high flow rate), partially closed (low full rate), or fully closed (off).

The ultrafiltration therapy is started at block 414 using the established control parameter setting(s). As described previously, the fluid status measurement is monitored during ultrafiltration at block 416 to allow further adjustment of a control parameter at block 420 as needed and to determine when a target level of the fluid status measurement is reached at block 418. Ultrafiltration continues at block 422 until the target level is reached at block 418, at which time ultrafiltration is stopped at block 424. The IMD continues to acquire and store fluid status measurements at block 404 to determine when ultrafiltration therapy is needed again.

Initially following an ultrafiltration session, the fluid status monitoring may be performed at block 404 in an acute mode in which fluid status measurements are obtained more frequently than in a chronic monitoring mode. The acute mode may be sustained for a specified period of time, for example, several hours or days. A notification is optionally generated at block 426 to notify the patient and/or a clinician that a target level has been reached and that ultrafiltration therapy has been or is being stopped.

As such, a fully automated, closed-loop method of regulating ultrafiltration therapy is contemplated in which the IMD (or other system component receiving IMD fluid status measurements) determines, based on fluid status measurements, when ultrafiltration needs to be started and stopped. A controller may further use the fluid status measurements to establish and automatically set ultrafiltration control parameters. It is recognized that in various embodiments, semi-automated methods may be implemented in which user-intervention is required, e.g. to enable data transmission, to enable an ultrafiltration unit to start operating, to set an established control parameter, to disable or stop the ultrafiltration unit operation, or the like.

After stopping ultrafiltration, the therapy session may be logged at block 428 by the IMD, a programmer, in the central database or by the ultrafiltration unit. The start and stop times and dates, control parameters used during therapy delivery and fluid status measurements obtained leading up to, during and after ultrafiltration therapy may be stored by the IMD or another system memory to provide diagnostic and prognostic data to a clinician for managing the patient. Such data may be used in setting the fluid status measurement target range, target level, therapy threshold (if different than a target range boundary), and in establishing ultrafiltration control parameters. Such data storage may further include documentation of patient symptoms to allow indication of fluid overload or volume depletion (for example by over-diuresis) to be correlated to the fluid status measurements and control parameters. This information may be used by the clinician or by the medical device system automatically to adjust a therapy threshold, target level, target range or control parameters, for example, if the patient shows signs of hypovolemia subsequent to the ultrafiltration therapy, if the frequency of ultrafiltration therapy is high due to early crossing of a therapy delivery threshold after ultrafiltration therapy, or if the patient experiences hypervolemic symptoms earlier than expected after ultrafiltration.

Thus, methods and associated apparatus for regulating ultrafiltration therapy have been presented in the foregoing description with reference to specific embodiments. It is appreciated that various modifications to the referenced embodiments may be made without departing from the scope of the invention as set forth in the following claims.

We claim:

1. A method for use in a medical device system comprising a physiological sensor and an ultrafiltration therapy delivery device, the method comprising:
   sensing at least one physiological signal from an implanted medical device (IMD) in a patient;
   computing a fluid status measurement of the patient using the at least one physiological signal;
   delivering ultrafiltration therapy to the patient according to a therapy delivery control parameter; and
   establishing a setting for the control parameter in response to the fluid status measurement;
   wherein the at least one physiological parameter includes an ECG signal.

2. The method of claim 1, further comprising:
   storing a target range of the fluid status measurement;
   comparing the fluid status measurement to the target range; and
   establishing the control parameter in response to the comparison.

3. The method of claim 2, further comprising determining a trend of previously computed fluid status measurements and computing the target range using the trend.

4. The method of claim 2, wherein establishing the control parameter comprises establishing a flow rate in proportion to a difference between the fluid status measurement and the target range.

5. The method of claim 4, wherein establishing a flow rate comprises controlling one or more valves to control the flow rate.

6. The method of claim 2, further comprising storing a target level of the fluid status measurement,
   performing ultrafiltration until a current fluid status measurement reaches the target level.

7. The method of claim 2, further comprising sensing at least a second physiological signal in the patient; wherein the first physiological signal and second physiological signal are different signals; computing a second fluid status measurement of the patient using the second physiological signal; and wherein the target range is an index computed using a combination of the at least two fluid status measurements.

8. The method of claim 1, further comprising storing a therapy delivery threshold;
   comparing the fluid status measurement to the therapy delivery threshold and detecting a need for ultrafiltration therapy in response to the comparison;
   enabling the ultrafiltration therapy delivery device in response to detecting the need.

9. The method of claim 1, further comprising:
   computing an updated fluid status measurement during delivery of ultrafiltration therapy; and
   determining an adjusted setting for the control parameter in response to the updated fluid status measurement.

10. The method of claim 9, further comprising stopping ultrafiltration therapy when the updated fluid status measurement is within a target range.

11. The method of claim 1, further comprising sensing at least a second physiological signal in the patient; wherein the first physiological signal and second physiological signal are different signals;
   computing a second fluid status measurement of the patient using the second physiological signal; and
   wherein the step of establishing a setting for the control parameter in response to the fluid status measurement comprises establishing a setting for the control parameter in response to the first and second fluid status measurements.

12. The method of claim 11, wherein the second physiological signal is selected from the group consisting of intraventricular pressure, thoracic impedance, oxygen, blood urea nitrogen, serum creatine, serum electrolytes, blood glucose, thyroid stimulating hormone, intracardia right ventricular pressure signals, transthoracic signals, or any combination thereof.

13. The method of claim 1, wherein the control parameter is a setting which enables or disables ultrafiltration.

14. The method of claim 1, wherein the control parameter is pressure across an ultrafiltration membrane.

15. The method of claim 1, wherein the ultrafiltration therapy delivery device automatically delivers ultrafiltration therapy to the patient when the fluid status measurement is outside of a target range.

16. The method of claim 1, wherein the ultrafiltration therapy delivery device generates a notification when the fluid status measurement is outside of a target range.

17. The method of claim 1, further comprising a step of continuously decreasing or decreasing in small stepwise increments the control parameter, as the fluid status measurement improves.

18. A computer readable medium storing a set of instructions which cause a programmable processor implemented in a medical device system comprising a physiological sensor and an ultrafiltration unit to perform a method comprising:
   sensing at least one physiological signal from an implanted medical device (IMD) in a patient;
   computing a fluid status measurement of the patient using the physiological signal;
   delivering ultrafiltration therapy to the patient according to a therapy delivery control parameter; and
   establishing a setting for the control parameter in response to the fluid status measurement;
   wherein the at least one physiological signal includes an ECG signal.

19. The computer readable medium of claim 18, wherein the method further comprises determining a trend of previously computed fluid status measurements and computing the target range using the trend.

20. The computer readable medium of claim 18, wherein the method further comprises sensing at least a second physiological signal of the patient; computing a second fluid status measurement of the patient using the second physiological signal; and
   wherein the step of establishing a setting for the control parameter in response to the fluid status measurement comprises establishing a setting for the control parameter in response to the first and second fluid status measurements.

21. The computer readable medium of claim 20, wherein the second physiological signal is selected from the group consisting of intraventricular pressure, thoracic impedance, oxygen, blood urea nitrogen, serum creatine, serum electrolytes, blood glucose, thyroid stimulating hormone, intracardia right ventricular pressure signals, transthoracic signals, or any combination thereof.

* * * * *